United States Patent [19]

Popp et al.

[11] Patent Number: 5,426,054
[45] Date of Patent: Jun. 20, 1995

[54] PROCESS AND APPARATUS FOR DETERMINING AN OPTIMAL ENERGY INSERTION IN COAGULATING SYSTEMS

[75] Inventors: Peter Popp, Pirna; Ulf Weber, Radeberg, both of Germany

[73] Assignee: Haake Medingen GmbH, Medingen, Germany

[21] Appl. No.: 121,378

[22] Filed: Sep. 15, 1993

[30] Foreign Application Priority Data

Sep. 16, 1992 [DE] Germany .............. 42 31 020.2

[51] Int. Cl.$^6$ .............. G01N 21/01; G01N 21/85
[52] U.S. Cl. .............. 436/70; 436/165; 422/73; 422/82.09; 73/61.71; 73/64.41; 356/427; 356/433; 356/435; 356/442
[58] Field of Search .............. 422/73, 82.05, 82.09; 436/165, 70; 356/427, 433, 435, 440, 442; 73/60.11, 61.71, 64.41

[56] References Cited

FOREIGN PATENT DOCUMENTS

4036048A1  5/1991  Germany .

OTHER PUBLICATIONS

Toshia Tanaka et al., Japan; "Optical Absorption Studies of the Growth of Microcrystals in Nascent Suspensions", pp. 213–219; *Society of Photographic Scientists and Engineers;* vol. 20, No. 5, Sep./Oct. 1976.
Otto Helmboldt and Dipl.-Ing. Walter Vogel, Germany; "Beurteilung von Flockungsvorgaengen", *Wasser, Luft und Betrieb 13 (1969), Nr. 5;*
Prof. Dr. W. Stumm and Dr. H. Hahn, Harvard University, USA; Publication of 2nd Lecture Series with Discussion of Karlsruhe University, Germany; Heft 3, 2. Vortragsreihe mit Erfahrungsaustausch ueber spezielle Fragen der Wassertechnologie:-Flockung-1967.
Dr. K. Haberer, Wiesbaden, Germany; Publication of 2nd Lecture Series with Discussion of Karlsruhe University, Germany; Heft 3, Teil II, 2. Vortragsreihe mit Erfahrungsaustausch ueber spezielle Fragen der Wassertechnologie:-Flockung-1967.

*Primary Examiner*—David A. Redding
*Attorney, Agent, or Firm*—Griffin, Butler, Whisenhunt & Kurtossy

[57] ABSTRACT

A determination of optimal energy insertion, or input, results from a measurement of opacity at various heights in a fluid coagulating system and at the same time from measuring a deviation width of the opacity at a lower measuring point. Simultaneously, a continuous comparison takes place of the opacity measured at the various measuring points, which changes with time, and a comparison of the deviation width of opacity. The optimal energy insertion in the fluid coagulating system is achieved if, at each point in time, the opacity at all measuring points is maintained approximately the same and the deviation width of the opacity is maintained at or near a maximum.

11 Claims, 2 Drawing Sheets

PROCESS AND APPARATUS FOR DETERMINING AN OPTIMAL ENERGY INSERTION IN COAGULATING SYSTEMS

BACKGROUND

This invention concerns a process and an apparatus for determining optimal energy insertion into coagulating systems, particularly for precipitation, floccing, and sedimentation processes, by means of opacity measurements, so that, without great chemical, energy, and time expenditures, processes for precipitating, floccing and sedimentation, for example for preparation of drinking water or for cleaning industrial or communal sewage and similar processes in the chemical industry, can be designed, evaluated and optimized.

Known processes and apparatus to investigate precipitation, floccing (or coagulation), and sedimentation behavior have not taken into consideration kinetic energy which in actual processes is applied to fluid coagulating systems.

Because of rising demands for protecting the environment, increasing application is made of processes of precipitation neutralization, processes of floccing, and related processes of sedimentation for cleaning drinking water as well as for cleaning sewage, so as, for example, to eliminate phosphates from community-sector sewage or to remove heavy metals from industrial sewage.

To design new installations or to technically optimize processes of existing installations, because of the complexity of courses, or sequences, of such processes, it is essential to carry out, beginning with laboratory measures, tests with which technical parameters of the processes for operating the installations can be determined.

In addition to an analytical determination of materials contained in water before and after treatment, so-called series, or multiple, stirring works have been employed for decades in which simultaneous multiple tests under varying particular parameters were carried out (Haberer, K.: "Moeglichkeiten und Grenzen der Steurung von Flockungsanlagen," published by the Abteilung des Lehrstuhls fuer Wasserchemie, Pamphlet 3, Institut fuer Gastechnik, Foerderungstechnik und Wasserchemie of the Universitaet Karlsruhe, Karlsruhe, 1967/1).

The variation of a test parameter is limited in this exclusively to the amount of floccing compound. All additional test conditions are intentionally held constant. In particular, the mixing, or stirring, speed or stirring energy is not brought into consideration as an influential parameter. The described variations of rotational speed is in two steps, one for the usual method of floccing testing to first achieve a quick and uniform distribution of the floccing compound in the medium and, thereafter, one to maintain the uniform distribution. In each case the stirring rotational speed is held constant in each phase.

The evaluation of the precipitation, floccing, and sedimentation course thereby results mainly through subjective visual assessments using arbitrarily chosen rigged scales, which leads to tests which are carried out at different places by different people which cannot be compared. Thus, an actual documentation of an entire course of such a process is not thereby achieved.

In general, the employment of multiple stirring works, or devices, serves to allow a comparison of end results of tests which have been carried out in parallel. A change of the process parameter "mixing energy" is not achieved thereby. More importantly, only variations in the amount of concentration of floccing compound or auxiliary material are used.

Particle counting apparatus are further known with which the number and size of colloid particles can be determined when they flow through a test opening. These devices however fail when used with randomly divided flakes, or flocs, of various different structures and combinations, as they are in actual floccing processes.

Along the same lines, an apparatus is described by TANAKA AND MATSUBARA (Optical Absorption Studies of the Growth of Microcrystals in Nascent Suspensions, Silver Chloride Hydrosols, 1976, pg. 213-219 /2/) with which, by means of an optical sender and receiver, the light transmission of a fluid mixture, or solution, can be determined. With this apparatus an opacity measurement is carried out in which the height of the opacity limits is determined as a measure of the concentration of silver chloride in the solution. In order to distribute precipitated silver chloride uniformly in the suspension, a high-speed magnetic stirrer is used which inevitably breaks apart developing flakes to achieve a uniform distribution. In this respect, the authors themselves write that such an apparatus is only suitable for nascent liquid mixtures. By operation of the apparatus, an assessment of a beginning stage of a nucleating agent (the beginning of the peri-kenetic phase) is possible. A description of an entire precipitation, floccing, and sedimentation course, or sequence, in an actual fluid mixture (for example sewage) is not possible with this apparatus.

An evaluation of the floccing behavior at various points in an reaction container, for example at various heights, is also not possible with this arrangement.

A further method is described in German Offenglegungsschrift DE-OS 40 36 048 /3/ with which a determination of a foam height or sedimentation height in a fluid can result. The opacity increase of the optical density of foam and sedimentation borders serves thereby to provide a characteristic measurement for determining foam and sedimentation heights. Floccing and the sedimentation results without additional introduction of kinetic energy through only the force of gravity. With this process and the described apparatus therefor, only a determination of an end condition of a precipitation and sedimentation process is possible. Also, this described process requires at least two test runs carried out in series because first a calibration of the test arrangement and, only thereafter, an optical determination of the vertical layer borders (opacity increases) at foam and sedimentation layers must be carried out. A continuing analysis and documentation of the entire precipitation and floccing process is not possible with this solution. However, this process allows a determination of a speed of sedimentation and a height of the sedimentation in a reaction container.

In 1969, through HELMBOLDT AND VOGEL (Helmboldt, O.; Vogel, W.: Beurteilung von Flockungsvorgaengen, Wasser Luft und Betrieb 13 (1969) 5, pages 164-168) a substantial systematizing of the observation and documentation of precipitation, floccing, and sedimentation processes resulted, in that they described the optical manifestations of these processes by means of opacity measurements taken throughout an entire test run in a 600 mm becher glass. From obtained opacity curves, valuable conclusions as to the test parameters can be gained. From this the dynamic course, or sequence, of a precipitation, floccing and sedimentation process can be described as follows:

After the mixing of a floccing compound, with a conventional stirrer, into a liquid to be examined (so-called mixing phase) it (the mixture) enters a floccing phase in which there is intimate contact between the floccing compound and the suspended impurities. A distinct floccing increase leads to an increase in the opacity of the fluid. Thereby an increase in the opacity in relation to the beginning opacity serves as a measure of the intensity of the precipitation process. In a similar manner, a difference between the beginning and the end opacities is a measure of a cleaning effect. The schematic representation of the course, or curve, of opacity in an actual floccing process is represented in FIG. 1.

This analyzing method is burdened by a list of disadvantages:

For optimum floccing, conditions are assumed which create maximum large flocs, or flakes, which are maintained in suspension by insertion of appropriate stirring energy without, however, being destroyed by shearing forces created by the stirrer. This condition must be maintained in a stable manner over a sufficient time span to allow the flakes, or flocs, to partly absorb on their outer surfaces, from the surrounding fluid, released molecules as well as dispersed colloid particles, with the goal of achieving maximal cleaning effect. Because this optimum itself depends upon many parameters, such as concentration of the contained material, electrolyte content, concentration and insertion point-of-time of the precipitation, or floccing, compound, and the density and size of the flocs and because it can be shifted during the floccing process, it is often necessary with the above-described apparatus to have a large series of preliminary tests to approach an optimum energy insertion. To date, there are no known laboratory processes or apparatus which make possible optimizing floccing processes, relative to energy insertion, which are practically and technically controllable, and which react to changes in process parameters.

Theoretical calculations of an optimum energy insertion using opacity measurements are not possible because of the various characteristics of water contained materials with regard to its chemical composition, their various sizes concentrations, and colors, their various geometrical shapes, their various and different basic characteristics and their variety of different physical-chemical parameters.

A controlling of temperature by means of a thermostat on a test reactor, and thereby the possibility of carrying out comparative tests at various temperatures, was not realizable by Helboldt and Vogel without disturbing feedback effects on the measured results because, upon transmitting light through a sleeve about the reactor and a thermostatic liquid, the intensity of a light beam would be falsified, particularly by means of such influences as opacity and pollution of the thermostatic liquid and gradually appearing sedimentation on an inner surface of the sleeve of the thermostatic container, which would lead to unreproducible measured results.

Upon very voluminous flocculation the upper sedimentation border remains over a fixedly installed light gate, which obstructs transmission of the light. An evaluation in a test, with such a total extinction, is no longer possible.

In addition to the precipitation, floccing, and sedimentation, a process engineer is also interested in the characteristics of the flakes, or flocs, which, for example, for a specific filter counter-resistance finds its expression as an important characteristic for the drainage of sediment. For such an investigation, withdrawal of the sediment is necessary. The sucking out the flocs sediment by means of a syphon or pipette from a floor of a becher glass leads however, through the appearance of shearing forces, to an intermediate destruction of the flocs which, when stationary, can build themselves back, however, in the rule they then display other geometry and changed characteristics.

Normal laboratory stirrers, in leaf or propeller form, lead to the appearance of substantially higher energy, or shear, gradations in areas of stirring edges than at areas spaced large distances from the stirring element, for example near a container wall or at a floor space of a reactor. This can lead to, already during the floccing process, a partial, and partly irrevsible, breaking up of the flocs. Because of this, the characteristics of the flocs sediment, have a negative influence on the drainability and absorption properties for other released or colloidal distributed water contained materials.

It is an object of this invention to provide a process and a measuring apparatus for carrying it out which make possible the duplication of complex dynamic precipitation, floccing and sedimentation processes as well as the analyzing, and the optimizing of relevant process parameters thereof. At the same time, a transferring of the resulting optimized process parameters to small as well as to large technical processes should be possible.

SUMMARY

According to principles of this invention, the opacity of a coagulating fluid system in a reactor is determined at at least two different heights and at the same time, at a lower measuring point, a deviation width of the opacity is determined, accordingly a continuous comparison of the time-wise changing opacities at the heights of the individual measuring points is made and, at the same time, a comparison of the changes of the deviation width of the opacity as a function of time is made and finally the insertion of stirring energy into the coagulating fluid in the reactor, to maintain a suspended condition of particles, is changed so that at each point of time at which a reading is taken the opacity is the same at all measuring points and the deviation width of the opacity, at the same time, is a maximum.

Other objects of the invention and the manner of making and using it will become obvious upon consideration of the following description and the accompanying drawings.

DETAILED DESCRIPTION OF A PREFERRED EMBODIMENT

Figure 1:
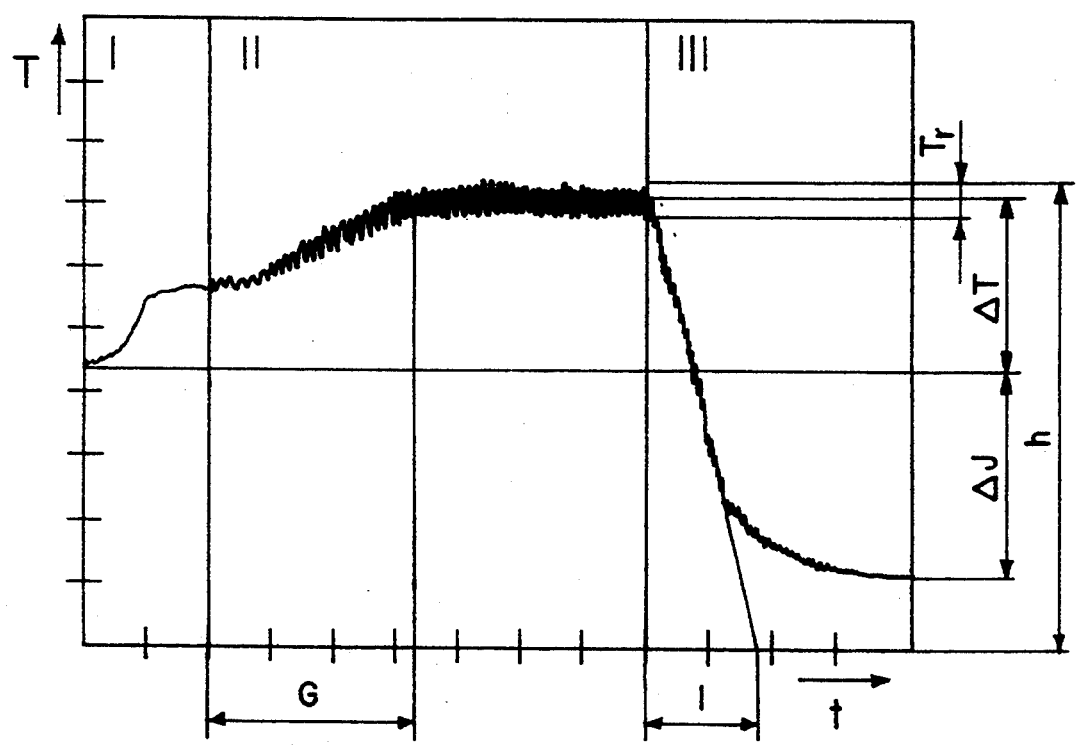
FIG. 1 is a schematic diagram of a graph depicting the course, or curve, of opacity in an actual precipitation, floccing and sedimentation process.

A test course, or sequence, (FIG. 1) is divided into three phases:

In the first, phase (I), a floccing compound is vigorously stirred into a fluid, or liquid, mixture. In phase (II), an intensive growth phase, a defined insertion of stirring energy takes place in order to create the largest possible flocs, or coagulum, and maintain created flocs in a suspended state (an orthokenetic transport phase). In this regard, the intensity of the floccing ($\Delta T$) and the size of the flocs can be read, or monitored by means of the swings, or deviation, width (Tr) of the opacity. According to the invention, the intensity of the floccing $\Delta T$ is measured at at least two, arranged one above the other, light gates, or monitors, and it is set via a control loop, to a uniform value by changing the amount of energy inserted into the system. The energy insertion is additionally influenced, by means of the deviation width Tr of the opacity so that the flocs sizes should reach a maximum;, that is, the deviation width Tr of the opacity become a maximum. In the third phase (III), by sedimentation, there is no more insertion of stirring energy. Here a conclusion with regard to a cleansing effect ($\Delta J$) and to sedimentation, or sedimentation ability (relationship h/I) can be made.

Figure 2:
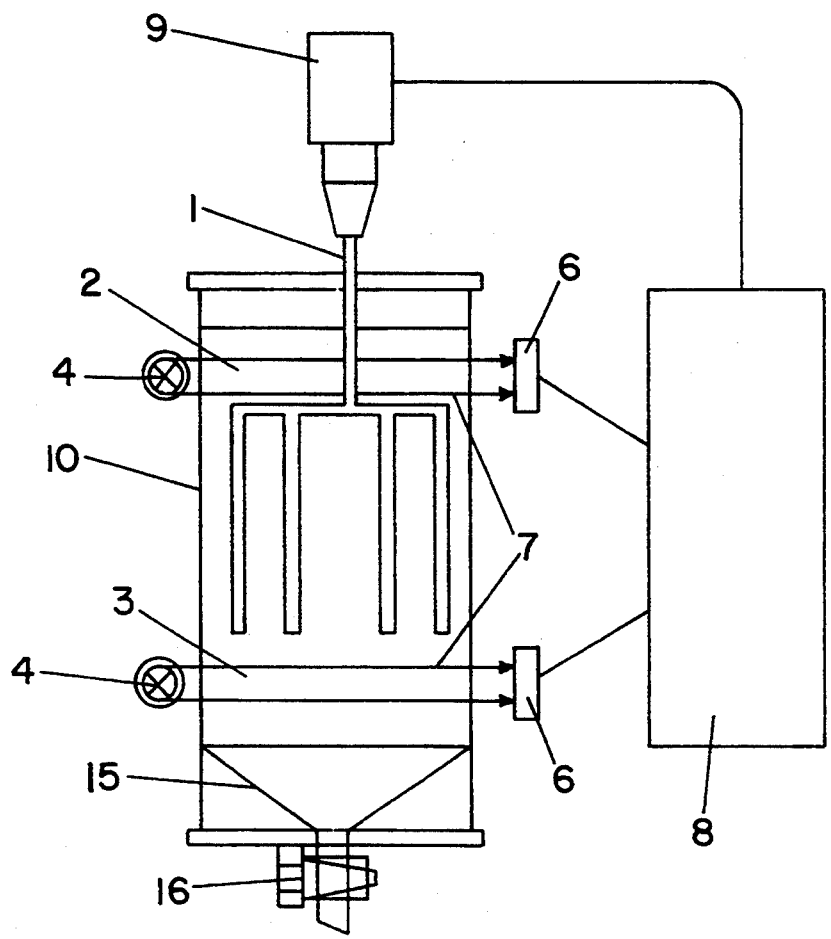
FIG. 2 is a schematic side view of an apparatus of this invention for performing a process of this invention as represented by the graph of FIG. 1; and, FIG. 3 is a schematic top view of a reactor container of the apparatus of FIG. 2.

A preferred method of realizing this process in a laboratory results by using a temperature controlled precipitation apparatus (FIG. 2), in which the opacity in lower and upper areas of a core, or main, zone of floccing, or floc build-up, is measured and, by means of an actual/desired comparison, the rotational speed of a stirrer (1) is adjusted so that the opacities in the lower and upper areas of opacity measurement are the same and, at the same time the deviation width of the opacity is at a maximum. In addition to keeping data on opacity (FIG. 1) the stirring energy over an entire course of the floccing phase is also recorded. Its calculation thereby results from the rotational speed of the stirrer when taking into consideration a viscosity of the liquid at a respective test temperature. Determination of the opacity value and the swing, or deviation, width of the opacity results from operation of two light gates 2 and 3 each of which comprises illumination optics, or a light source, 4 on one side and a photosensor 6 positioned opposite thereto. The measured values are fed to a microprocessor-controlled adjusting member 8 which changes the rotational speed of a stirring motor 9 until both conditions are fulfilled.

Figure 3:
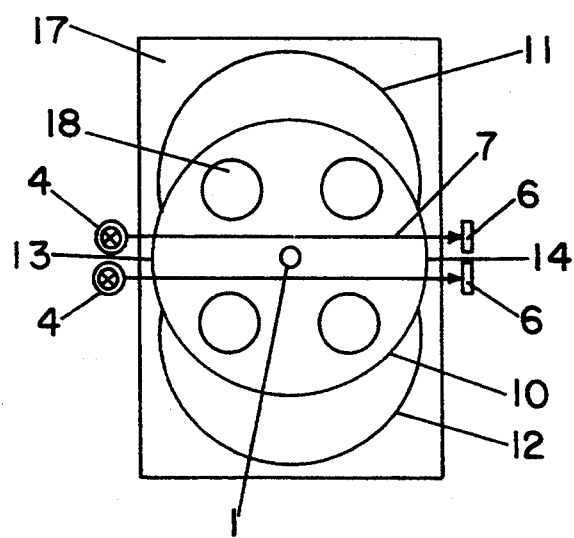

In a further preferred embodiment (FIG. 3) the apparatus comprises a reactor 10 whose thermostatic envelope 11 and 12 is placed on the reactor 10 in a split shell form so that there are two vertical slots, or spaces, 13, 14 formed diametrically opposite to one another through which beams of the light gates 2 and 3 can pass through the reactor without being hindered by thermostatic envelope material or by gathered sedimentation, or opacity, of thermostatic fluid.

Both light gates 2, 3 are arranged so that light beams therefrom are not broken by movement of the stirrer 1 and both light beams have the same horizontal-path length through the medium to be analyzed. The upper light gate 2 has a minimum displacement from a top surface of the examined floccing suspension which is sufficiently great that, a total reflection at the top surface of the liquid, does not cause reflected disbursed-light of particles to reach the upper photosensor.

The lower light gate 3 is arranged above a sedimentation border and has a minimum vertical spacing from this which is so chosen that reflected disbursed light of particles therefrom does not reach the lower photosensor. In this regard, the lower light gate 3 is arranged to be adjustable along the vertical slots, or spaces, 13, 14 so that its height can be adjusted to suit an expected sedimentation border. However, within these parameters, the light gates 2 and 3 are spaced a maximum vertical distance from one another.

A reactor floor 15 is funnel shaped, constructed to have an opening angle of between 95° and 115° and is provided with a closable floor drain 16 so that sedimentation sediment, which falls out, can be carefully, and gently, sucked out and lead away for further examination. A cover 17 of the reactor has openings 18 which make possible, by means of additional sensors the recording of, for example, temperature, Ph value and ion concentration.

The stirrer is so formed and arranged that a uniform stirring energy results over an entire reactor interior space without light beam transmissions of the optical system being disturbed. In a preferred embodiment, the stirrer has the form of a four-pronged fork whose perimeter measurements are 50% to 70% of a reactor diameter and 40%–60% of a reactor height, with the perimeter cross measurement of the fork prongs being 4 mm–6 mm.

By means of the divided thermostatic envelope for the apparatus an optical imparement of analytical results, by possible sedimentation on the thermostatic envelope's interior walls and opacity of the thermostatic fluid, is avoided. That is, the thermostatic envelope, or sleeve, has the shape of a two-piece shell which at its fastening lines to both sides of the reactor, leaves a negligibly small, relative to heat radiation, slot through which light beams can be transmitted, undisturbed by outside influences. In this regard, a possibility is provided for moving and fixing at various heights, the lower optical light gate, which comprises respectively a light source and a photosensor, along this slot, whereby the height of this lower measuring device can be adjusted to respective expected different heights of sedimentation surface borders for various test conditions.

A procedural, technical, overall evaluation of the measured results and an optimization of an overall installation can only be carried out when one successfully removes created flocs sediment from the apparatus in such a manner that flake or flocs, geometry will not be possibly damaged, which would make, for example, a determination of a particular filter counter-resistance impossible. The arrangement of the floor drain, therefore, is in the shape of a blunted cone whose angle at a point thereof is 95°–115°. If the angle is too flat a friction produced shearing stress at the cone wall is too great. If the angle is too pointed, the stirring energy during the floccing phase is not sufficiently uniformly transmitted over the entire reactor.

If the necessary stirring energy is put in by means of a normal laboratory stirrer of a leaf or propeller type, large energy and shear gradations result depending upon a distance of a respective reactor space from an edge of the stirring element, which can also lead to a partial, irreversible, breaking or smashing of developed flocs. To avoid this effect the stirrer was developed to have a fork form which fills out the reactor volume sufficiently that, on the one hand, only small local energy differences appear and, on the other hand, however, the light cones passing through the reactor are not thereby disturbed.

By means of the following application examples the invention is more particularly described.

EXAMPLE 1

A city waterworks that produces drinking water from shore filtrate by means of aluminum sulfate floccing wishes to determine how seasonal cooling of raw water in winter, which cooling causes a slowing of reactions and thereby leads to an employment of higher amounts of chemicals, can be compensated for by the use of inorganic floccing compounds.

To do this a 2.5 liter capacity laboratory reactor of the described construction is used with, as light sources, two incandescent, or filament, lamps 6 volt 10 watts. For each individual test, a particular temperature of the shore filtrate is set by means of a thermostat. The concentration of added inorganic flossing compound is varied for a predetermined temperature. A stirring speed "hunts" to a steady state of, depending on the amount of floccing compound, from 12 to 19 turns per minute. By comparing individual test curves the concentration of the inorganic floccing compound will be increased until there is no more increase in the opacity, as an expression of the floccing intensity, and no more increase in the slope of the decent curve, as an expression of the sedimentation speed. By this optimizing of the overall installation an excessive use of inorganic floccing compound is prevented, whereby substantial expenditures can be prevented. At the same time, a renewed dispersing of already flocculated contained material, which is brought about by too high floccing compound concentrations, can be prevented.

EXAMPLE 2

In an industrial sewage cleaning installation heavy metals are to be precipitated from mixed sewage by means of calcium hydrate. Feeding back freshly precipitated purified sediment has been proven to improve this reaction. Laboratory tests are carried out with the apparatus of Example 1. Since, however, a substantially higher flocs concentration is to be expected in the reactor than during preparation of drinking water, instead of two light sources 6 volt, 10 watt, two lamps 6 volt, 25 watts are used. The amount and age of the admixed contact sediment is changed. The stirring speed sets itself, depending upon the amount of the admixed contact precipitate, because of the heaviness of the developed flocs, between 37 and 45 rotations per minute. An optimum is achieved if the size of the created flocs, characterized by the swing, or deviation, width of the opacity curve (teeth) and the slope of the descent of the opacity curve as an expression of good sedimentation, no longer increases. By operation of the installation at this optimum, a large amount of pump energy can be saved.

EXAMPLE 3

A floccing compound manufacturer wishes to objectively evaluate the effectiveness of newly developed floccing compounds, which are designed for sewage treatment at industrial sewage purification installations. The test apparatus is substantially identical with that of the described apparatus for Example 2. The course, or progress, of precipitation, floccing, and sedimentation curves, upon employment of different organic floccing compounds allows an evaluation as to which floccing compounds, significantly influence the respective precipitation and floccing process. Subsequent further tests to optimize the concentrations to be employed will be carried out with those effectively developed substances.

A final large test in an industry installation is only necessary for a floccing compound which has been optimized by laboratory tests of the type described, whereby expenses and development time are substantially reduced.

While the invention has been particularly shown and described with reference to preferred embodiments, it will be understood by those skilled in the art that various changes in form and detail may be made therein without departing from the spirit and scope of the invention. For example, a determination of the opacity of coagulating fluid systems containing particular pollutants with particles of various color spectrums can be carried out with white light at the light gates 2 and 3.

The process and the apparatus to determine the optimal energy insertion can be beneficially used for optimizing precipitation, floccing, and sedimentation processes, particularly for preparing drinking water, for cleaning communal sewage, or for getting rid of heavy metal from industrial sewage. Similarly, in an uncomplicated manner, simulated models for testing the effectiveness of newly developed floccing or floccing compounds can be carried out.

The embodiments of the invention in which an exclusive property or privilege are claimed are defined as follows:

I claim:

1. A process to determine an optimal energy insertion into a fluid coagulating system in dependence on physical and chemical process parameters by means of opacity measurements, particularly during precipitation, floccing and sedimentation processes when preparing drinking water, cleaning communal and industrial sewage and performing precipitation and floccing processes in the chemical industry, said process including the steps of:
   containing the fluid coagulating system in a test reactor and measuring the opacity of the fluid coagulating system in the test reactor at at least two different measuring heights while simultaneously determining a deviation width of the opacity at one of the two different measuring heights;
   comparing opacity measurements taken as a function of time at different measuring heights and comparing the deviation width of the opacity at a particular point in time with the deviation width of the opacity a different point in time; and,
   inserting a mixing energy into the fluid coagulating system; and,
   changing this inserted mixing energy for creating flocs and maintaining flocs suspended in an orthokinetic transport phase such that the opacity is maintained approximately the same at all measuring heights and the deviation width of the opacity is maintained at or near a maximum.

2. A process as in claim 1 wherein a determination of the opacity and its deviation width is made by passing light beams through the fluid coagulating system whereby the light beams are parallel or cone-shaped and a light attenuation brought about by flocs suspended in the fluid coagulating system is measured by photo-sensors.

3. A process as in claim 1 wherein a determination of the opacity of mixed pollutants, and particularly pollutants with particles having various color spectrums, is carried out with white light.

4. An apparatus for performing a process to determine an optimal energy insertion into a fluid coagulating system in dependence on physical and chemical process parameters by means of opacity measurements, particularly during precipitation, floccing and sedimentation processes when preparing drinking water, cleaning communal and industrial sewage and performing processes in the chemical industry, said apparatus comprises:
- a light transmissive reactor for containing the fluid coagulating system which is surrounded by a thermostatic envelope which defines diametrically opposite vertical slots therein;
- at least upper and lower light gates each comprised of an illumination optic for sending a light beam through the light transmissive reactor at said slots and a photo-sensor for receiving the light beam which are positioned on opposite sides of the reactor and which are approximately horizontally aligned with one another, with the illumination optic and the respective photo sensor of the lower light gate being adjustable in a vertical direction;
- a stirring motor for driving a stirrer in the reactor via a drive shaft;
- a microprocessor-controlled adjustment member coupled to the photo-sensors and to the stirring motor which monitors the opacity determined at the photo-sensors caused by suspended flocs in the examined fluid coagulating system and controlling the stirring motor in response thereto;
- wherein the magnitude of the opacity, as measured at all photosensors, are compared and at the same time the deviation width of the opacity at a point in time is compared to that at a different point in time and, via the microprocessor-controlled adjustment member, the rotational speed of the stirring motor is changed in dependence on the measured opacity so that the opacity measured at all photosensors is approximately the same and, simultaneously, so that the deviation width of the opacity is at or near a maximum.

5. Apparatus as in claim 4 wherein the light gates are arranged so that all light rays travel a horizontal path of approximately the same length through the examined fluid coagulating system.

6. An apparatus as in claim 4 wherein the light gates are arranged such that the light rays are not broken by movement of the stirrer.

7. Apparatus as in claim 4 wherein the vertical distance between the lower and the upper light gates is a maximum with the upper light gate being spaced a minimum distance from an upper surface of the examined fluid coagulating system which is sufficiently large that a total reflection at an upper surface of the fluid coagulating system does not cause reflected dispersed-light of particles to substantially reach the upper photosensor and the lower light gate is positioned above a sedimentation border and spaced therefrom a sufficient vertical distance that dispersed light of particles which is reflected from the border, does not substantially reach the lower photosensor.

8. An apparatus as in claim 4 wherein the light gates employ parallel beams or cone shaped beams of white, or monochrome, light to determine the opacity and the deviation width of opacity.

9. Apparatus as in claim 4 wherein the light gates employ white light to determine the opacity and the deviation width when the apparatus is used for mixed pollutants, particularly pollutants with particles of various color spectrums.

10. Apparatus as in claim 4 wherein a floor of the reactor container is a cone-shaped funnel with an opening angle of between 95° to 115° which is provided with a closable floor drain for gentle removal of sedimentation.

11. Apparatus as in claim 4 wherein the stirrer has the shape of a multiple pronged fork with a measurement from side edges of the fork to a stirring axis being approximately 50 to 70% of a radius of a reactor interior space and the fork height being approximately 40% to 50% of the height of the reactor interior space for achieving a uniform insertion of stirring energy substantially in the entire reactor interior space.

* * * * *